United States Patent
Shaffer et al.

(10) Patent No.: US 7,022,234 B2
(45) Date of Patent: Apr. 4, 2006

(54) METHOD FOR BIOLOGICAL TREATMENT OF ENVIRONMENTAL CONTAMINANTS AND WASTE

(75) Inventors: Jon Shaffer, Huntington, NY (US); Jack Fernandes, Setauket, NY (US); John Lucido, Rocky Point, NY (US)

(73) Assignee: Aqua-Nova LLC, Plainview, NY (US)

( * ) Notice: Subject to any disclaimer, the term of this patent is extended or adjusted under 35 U.S.C. 154(b) by 0 days.

(21) Appl. No.: 10/218,947

(22) Filed: Aug. 13, 2002

(65) Prior Publication Data
US 2003/0029793 A1  Feb. 13, 2003

Related U.S. Application Data

(62) Division of application No. 10/043,056, filed on Jan. 8, 2002, now Pat. No. 6,982,032.

(60) Provisional application No. 60/260,586, filed on Jan. 9, 2001.

(51) Int. Cl.
*C02F 3/00* (2006.01)

(52) U.S. Cl. .................. 210/610; 210/205; 210/170; 435/262.5; 165/246

(58) Field of Classification Search .............. 210/205, 210/170, 610, 611; 435/262.5; 165/246
See application file for complete search history.

(56) References Cited

U.S. PATENT DOCUMENTS

| | | | |
|---|---|---|---|
| 4,670,149 A | 6/1987 | Francis | |
| 4,882,059 A | 11/1989 | Wong et al. | |
| 4,925,564 A | 5/1990 | Francis | |
| 4,940,539 A | 7/1990 | Weber | |
| 5,155,042 A * | 10/1992 | Lupton et al. | 435/262.5 |
| 5,171,687 A | 12/1992 | Moller et al. | |
| 5,225,083 A | 7/1993 | Pappas et al. | |
| 5,244,493 A * | 9/1993 | Brierley et al. | 75/743 |
| 5,271,829 A | 12/1993 | Heppenstall | |
| 5,340,376 A | 8/1994 | Cunningham | |
| 5,494,580 A | 2/1996 | Daskys et al. | |
| 5,577,558 A * | 11/1996 | Abdul et al. | 166/246 |
| 5,639,658 A | 6/1997 | Drobish et al. | |
| 5,840,182 A | 11/1998 | Lucido et al. | |
| 5,849,348 A | 12/1998 | Vinci et al. | |
| 5,888,395 A * | 3/1999 | Carman et al. | 210/606 |
| 5,955,323 A | 9/1999 | Chen | |
| 6,165,356 A * | 12/2000 | Carman et al. | 210/150 |
| 6,335,191 B1 | 1/2002 | Kiplinger et al. | |
| 6,355,449 B1 | 3/2002 | Chen et al. | |
| 6,402,941 B1 | 6/2002 | Lucido et al. | |
| 6,428,701 B1 | 8/2002 | Mullennix et al. | |

(Continued)

OTHER PUBLICATIONS

Grant & Hackh's Chemical Dictionary, McGraw Hill, 1987, p. 533 (absence of entry for "simethylcone".

(Continued)

*Primary Examiner*—Chester T. Barry
(74) *Attorney, Agent, or Firm*—Bryan Cave LLP (57) ABSTRACT

The invention is directed to an apparatus for delivering activated microorganisms to an environment to be treated. The apparatus has a bioreactor containing microorganisms, a supply of organic and inorganic nutrients and a controller. The controller maintains the conditions of the bioreactor so as to maintain the microorganisms in the exponential phase of growth. Although the apparatus is continuous, the controller also doses a portion of the fluid in the bioreactor to the environment to be treated. The invention also provides a method for the biological treatment of wastes and an organic and inorganic nutrient composition used to feed the microorganisms in the bioreactor.

7 Claims, 6 Drawing Sheets

U.S. PATENT DOCUMENTS 6,573,085 B1    6/2003    Lucido et al.

OTHER PUBLICATIONS

Results of US Patent EAST database text search of "simethylcone".

Internet search results on www.yahoo.com producing no answers to "simethylcone" search query.

International Search Report for PCT/US02/00341, dated May 30, 2002.

* cited by examiner

METHOD FOR BIOLOGICAL TREATMENT OF ENVIRONMENTAL CONTAMINANTS AND WASTE

CROSS-REFERENCE TO RELATED APPLICATIONS

This application is a divisional application of U.S. application Ser. No. 10/043,056, filed Jan. 8, 2002 now U.S. Pat. No. 6,982,032, and claims the benefit of U.S. Provisional Application No. 60/260,586 filed on Jan. 9, 2001.

FIELD OF THE INVENTION

The present invention relates to apparatuses and methods for biological purification of wastes. More particularly, the invention relates to apparatuses and methods for the treatment of wastes, such as grease, and other contaminants contained in waste water streams, ground water, soil, etc., by introducing pre-conditioned living organisms to the environment to be treated in order to biodegrade the waste.

BACKGROUND OF THE INVENTION

Wastes, under normal conditions, are gradually broken down or biodegraded by indigenous microorganisms in the environment. However, biodegradation reactions are often hindered by environmental fluctuations such as changes in temperature, pH, salinity, water and air supply, etc. For example, wastes such as fat and grease are biodegraded by microorganisms to fatty acids and glycerol. In the presence of oxygen the fatty acids are further metabolized with the end product being carbon dioxide and inert by-products. Glycerol is also metabolized as an efficient energy source.

Waste water systems, for example those in the food service industry, typically incorporate a grease trap to capture grease and other contaminants from the passing flow of wastewater and to store such contaminants for eventual removal from the trap. Typically, the grease trap is accessed periodically and the contaminants removed for eventual disposal. Grease and other contaminants often build up very quickly in such traps. If they are not removed in a timely fashion, the ability of the trap to operate efficiently, or at all, is seriously affected. When a trap is no longer functional, the contaminants will bypass the trap and flow into areas that are intended to be free from these contaminants. Specifically, the contaminants will either clog up the waste water system or will flow into the municipal sewer system in violation of local ordinances or state laws. Most grease traps require relatively large compartments, particularly if the associated food service facility operates on a large volume.

A variety of approaches have been developed to increase the required period between subsequent cleanings of a grease trap by increasing the bio-degradation by microorganisms of grease in the trap. One approach to enhancing bio-degradation of grease in a grease trap is to introduce chemicals or nutrients to the trap to aid naturally occurring bacteria or microorganisms in the trap. For example, U.S. Pat. No. 5,340,376 granted to Cunningham discloses a controlled-release nutrient source that adds nutrients at low levels to a biodegradation environment to enhance microorganisms' growth and activity and promote the effectiveness of the biodegradation in removing environmental contaminants. The nutrients are in the form of coated solid particles, each having a core of water-soluble microorganisms nutrients encapsulated in a release rate-controlling coating. The effectiveness of biodegradation of wastes by enhancing the growth of naturally occurring bacteria or microorganisms with the introduction of a controlled-release nutrient source is still hindered due to environmental fluctuations such as changes in temperature, pH, salinity, water and air supply, etc.

Another approach to enhancing bio-degradation of grease in a grease trap is to introduce a structure upon which indigenous microorganisms can bind and grow, and thus effectively remain in the grease trap. For example, U.S. Pat. No. 4,925,564 and U.S. Pat. No. 4,670,149 both granted to Francis disclose a bacterial incubator device having an enclosure with a foraminous wall structure packed with high surface area elements such as spherical packing of a shape or size to multiply the solid bacterial growth surface area in a grease trap. The incubator is positioned at the interface of floating grease and water. Similarly, the effectiveness of biodegradation of wastes by enhancing the growth of naturally occurring bacteria or microorganisms with the introduction of a support structure is often hindered due to environmental fluctuations such as changes in temperature, pH, salinity, water and air supply, etc.

Still another approach to enhancing bio-degradation of grease in a grease trap is to introduce additional microorganisms into the grease trap. For example, U.S. Pat. No. 5,271,829 granted to Heppenstall discloses a treatment system for wastewater that includes a dispenser for introducing treatment material, a solution of bacteria, into a grease trap for the purpose of digesting the grease that is separated from wastewater as it flows through the grease trap. The dispenser includes a housing having a compartment for holding a quantity of grease digesting material and a dispensing opening at the lower end of the compartment. A restrictor is located at the dispensing opening permitting the digesting material to pass at a constant restrictive rate from the dispensing opening to the grease to be treated in a chamber of the grease trap. The grease digesting material in the dispenser will naturally go through a four-phase growth cycle (i.e., lag, exponential, stationary, and death, further described in detail in a Bacterial Growth Section below) that limits its effectiveness of enhancing the bio-degradation of grease on an extended or continuous basis.

Another example of introducing additional microorganisms in to a grease trap is U.S. Pat. No. 5,225,083 granted to Pappas, et al. Pappas, et al. discloses a simple method that includes adding endemic bacterial microorganisms to one or more of the drain lines for ultimate introduction into the grease trap and biodegrading grease. Depending on the bacterial microorganisms' growth cycle phases, the effectiveness of the bio-degradation of grease by the microorganisms will vary.

Another approach to enhancing bio-degradation of grease in a grease trap is to introduce enzymes into the grease trap to solubilize the grease. For example U.S. Pat. No. 4,940,539 granted to Weber discloses a grease trap comprising a housing having an inlet to receive wastewater containing grease and an outlet. The wastewater within the housing is heated by an electric heating element that is immersed in the wastewater and the heating element is controlled by a thermostat to maintain a desired temperature of the water within a given range. An aqueous composition containing a mixture of enzymes and bacterial spores is introduced into the housing into contact with the wastewater. The enzymes solubilize the grease while the bacteria spores biodegrade the grease. However, the ability of the bacteria to biodegrade waste will be delayed in that the bacterial spores first enter a lag phase requiring a period of time before entering an exponential growth phase in which to begin bio-degradation of the waste.

Another example, U.S. Pat. No. 4,882,059 granted to Wong, et al. discloses a method for solubilizing particulate materials in waste water which comprises the steps of cultivating aerobic bacteria in the presence of oxygen in an activator solution containing a food source until the level of the food source drops below a predetermined level causing the bacteria to begin producing increased amounts of enzymes and thereafter contacting the activated bacteria and enzymes with the particulate materials under conditions which solubilize the waste. Another example, shown in U.S. Pat. No. 5,171,687 granted to Moller, et al., discloses an apparatus for culturing and delivering microbes for waste treatment in a flow system. The apparatus includes a container having a first and second chambers. The first chamber is maintained in a nutrient rich environment for the source microbial matter supported therein while the second chamber is nutrient deficient. Water is introduced into the first chamber at a predetermined rate and flows through an outlet into the second chamber. The outlet of the second chamber is directed to a flow system benefiting from the activity of the microbial matter. In both Wong and Moller, et al., it is believed that starving the bacteria of nutrients activates enzyme production therein to aid in solubilizing particulate materials in waste water. Although the enzymes aid in solubilizing the grease, the bacteria will be ineffective in biodegrading the solubilized grease in that the bacteria being nutrient deficient will enter a stationary phase (if not death phase) necessitating that the bacteria enters a lag phase, requiring a period of time before the bacteria enters an exponential growth phase in which to begin to biodegrade the grease. In addition, enzyme hydrolysis by itself is believed to merely cause intact fatty acids to be produced which are likely to redeposit further down the sewer lines causing even greater commercial environmental damage.

Another example, U.S. Pat. No. 5,840,182 granted to Lucido et al. discloses an apparatus for incubating microorganisms and delivering microorganisms to an environment containing waste for bio-augmenting the bio-degradation of waste. This apparatus comprises three separate containers each containing a specific content. The three containers are arranged in a specific orientation and this arrangement mandates a directed flow of fluid. The first container has a bioreactor vessel containing a bacterial culture. The second container has a chamber containing an aqueous solution of inorganic nutrients and a third container has a chamber containing an aqueous solution of organic nutrients. The third container being operably linked in a one-way fluid communication between the first container and the second container. The apparatus also contains a controller having a means for introducing a supply of the inorganic solution from the second container to the organic solution of the third container and a means for removing a portion of the bacterial culture from the first container and delivering it to the environment to be treated.

As stated above, the specific three container arrangement requires that the flow of aqueous inorganic solution in the second container be supplied to the organic nutrient containing third container. Once the inorganic solution of the second container mixes with the organic nutrients in the third container, a portion of the solution is supplied to the first container. The amount of inorganic nutrients provided to the third container from the second container is controlled by a pump in the controller. However, the amount of organic nutrients that dissolves in the aqueous inorganic solution supplied to the third container from the second container and then supplied to the first container, is not metered. Since the amount of organic nutrients that dissolves in the inorganic solution is affected by physical properties such as temperature pressure concentration etc., the amount of organic nutrients provided to the bioreactor will fluctuate as these physical properties fluctuate. This makes stabilizing fluid conditions in the bioreactor, so as to maintain the microorganisms in exponential growth, almost impossible. As a result, the microorganisms dosed to the environment to be treated by the controller are not always in the exponential phase of growth. Thus, the ability of the microorganism to biodegrade waste will diminish, causing system failures that may result in clogging and increased maintenance of the apparatus.

If the environment of the bioreactor changes and causes the microorganisms to exit the exponential phase of growth, in order to return the microorganisms back to the exponential growth phase (so as to be most productive in bio-degrading waste) restabilization of the bioreactor environment is required. In other words, stabilization of the aqueous environment in the bioreactor, including the amount of organic and inorganic nutrients, is required.

Assuming conditions can be stabilized, the microorganisms will still have to pass through a lag phase in order to return back to the exponential growth phase. If the amount of fluid, nutrients and/or the physical properties such as temperature, pH, salinity, etc., fluctuate during this period it will disrupt the re-stabilization process of the bioreactor and even further delay the return of the microorganisms to exponential growth. Any microorganisms dosed to the waste environment during this period will not be in the exponential growth phase and therefore will not actively bio-degrade waste.

Moreover, assuming that the microorganisms in the bioreactor return to the exponential growth phase, once the concentration of inorganic and organic nutrients fluctuate in the bioreactor, the microorganisms will again exit the exponential growth phase and the cycle will begin all over again. As a result, the waste in the environment being treated will not be bio-degraded and backups and clogs are likely to occur. As a result, waste may spill over into areas not intended for waste, and/or even cause waste to spill into the public sewage system in violation of local, state and/or federal laws.

There is a need for a waste bio-augmentation system for treatment of contaminants and waste products that is able to maintain the environment of the bioreactor, including the amount of fluid, organic nutrients, inorganic nutrients and other physical properties, so as to keep the microorganisms of the bioreactor in an exponential phase of growth. The microorganisms can then be delivered on a continuous or periodic basis to an environment containing contaminants and/or waste products for effectively bio-augmenting the bio-degradation of these contaminants and/or waste products. Such a system would require less maintenance and therefore be less expensive to operate. The present invention overcomes the shortcomings of existing systems.

SUMMARY OF THE INVENTION

The present invention provides a waste bio-augmentation system that adjusts the environment to be treated to a condition that is more conducive for bio-degradation of waste by introducing activated microorganisms designed for that purpose. Activated microorganisms are microorganisms that are in the exponential phase of growth. These microorganisms are more efficient in the biodegradation of waste than microorganisms that are not in the exponential phase of growth.

The present invention provides methods and apparatuses for the continuous culturation of evolving bacterial consortia and by-products for direct utilization in bioremedial and bioaugmentation applications, such that the digestion and mobilization of grease and/or other organic wastes in grease traps, pipes, and other septic and treatment systems or natural contaminated sites. The present invention also provides a nutrient media for feeding the continuous culturation of evolving bacterial consortia. The automated systems of the present invention enable long-term chemo static-like maintenance and growth of diverse consortia. The systems also enable semi-continuous dosing of target waste with activated, exponential phase microorganisms without intervention.

In general, the bio-augmentation system comprises an apparatus for delivering activated, pre-conditioned, microorganisms to an environment to be treated. The apparatus generally includes a bioreactor vessel, a nutrient reservoir source in fluid communication with the bioreactor vessel, a conduit coupled to the bioreactor vessel, and at least one pump in fluid communication with the bioreactor vessel.

One apparatus for delivering microorganisms to an environment to be treated of the present invention comprises a bioreactor comprising an output tube to the environment to be treated and a nutrient container comprising a mixture of inorganic and organic nutrients. The inorganic and organic nutrients are pumped from the nutrient container to the bioreactor by a nutrient pumping means. The nutrient pumping means is in fluid communication with the nutrient container and the bioreactor. The apparatus also includes a water pumping means for pumping water into the bioreactor. The water pumping means is in fluid communication with the bioreactor and a water source whereby the water pumped into the bioreactor displaces fluid out of the output tube of the bioreactor to the environment to be treated.

The present invention also provides an apparatus comprising a nutrient container comprising a mixture of inorganic and organic nutrients and a nutrient pumping means for pumping inorganic and organic nutrients from the nutrient container to the bioreactor. The nutrient pumping means is in fluid communication with the nutrient container and the bioreactor. The apparatus also includes a solenoid that is in fluid communication with the water supply and the bioreactor. The solenoid comprises both an open and closed position wherein water flows into the bioreactor when the solenoid is in the open position and water is prevented from entering into the bioreactor when the solenoid is in the closed position.

The present invention also provides methods for the biological treatment of wastes according to the present invention comprising continuously dosing a bacterial composition from an apparatus for delivering microorganisms to an environment to be treated. The methods us the apparatuses described above.

The present invention also provides a composition for feeding microorganisms in the bioreactor. The composition generally includes metal-oleate, $MgSO_4$, $CaCl_2$, $Na_2HPO_4$, ferric $NH$ citrate, $KHCO_3$, $NaCl$, Dextrose, Citrate, Yeast Extract, Whey Extract, $NH_4NO_3$, $NH_4Cl$, $CoCl_2$-$6H_2O$, $CuSO_4$, $Na_2EDTA$, Molybolic Acid, $MnCl_2$-$4H_2O$, $ZnSO_4$-$7H_2O$, Vitamin A, Vitamin D, Vitamin E, Vitamin K, Thiamin, Riboflavin, Niacin, Vitamin $B_6$, Folic Acid, Vitamin $B_{12}$, Biotin, Pantothenic Acid, Calcium, Iron, Phosphorous, Iodine, Magnesium, Zinc, Selenium, Copper, Mn, chromium, Molybdenum, Chloride, potassium, Boron, Nickel, Silicon, Tin and Vanadium.

DETAILED DESCRIPTION OF THE INVENTION

An apparatus according to the present invention comprises five main subsystems: a controller unit; a bioreactor; a potable water reservoir and regulator; pumping means and a nutrient container. Each subsystem constitutes a separate part of the invention.

A controller unit houses and protects electronic components and isolates electrical components, along with fuses and electrical boards, and connections for safe operation of the system and to comply with applicable standards. The controller is in communication with the other main subsystems of the apparatus. More specifically, the controller will regulate the function of the pumping system and/or the solenoid, and at least one timer. The solenoid is regulated by a timer and any pump(s) may be controlled by separate timer devices but are responsive to the at least one timer device. The types and numbers of pumps are not critical. For instance, a pump may be positioned to operate each input into the bioreactor, e.g. from water reservoir, nutrient container and atmosphere (to provide air to the bioreactor, for instance, to enable aeration). The pump may be a single multi-chambered pump or other appropriate pumping mechanism known in the art. The bioreactor provides an environment conducive for the culturation of microbes, and includes at least one container. The bioreactor may include one or more of the following: a heater (such as a thermostatically controlled heater), a temperature control, an aeration means, organic and inorganic nutrients, check valves for isolation of the bioreactor, and pipes and/or tubing to provide for aeration and for delivery of the nutrient formulation.

A potable water reservoir and volume regulator provides a regulated acclimatized supply of water for bioreactor. The reservoir and regulator also may operate to dampen external pressure events, isolate the potable water supply, and/or regulate the volume of water provided to the bioreactor through one or more pumps provided by the controller. The potable water reservoir includes a vessel and connecting tubes and/or pipes for communication with one or more pump and with the solenoid, and optionally may include a level sensor. The potable water reservoir may also include an air gap for overflow to the atmosphere, and the reservoir and regulator may also may be equipped with a water filtration device for preconditioning and/or microbial removal from the source water. The nutrient container may include one or more containers for containing organic and inorganic nutrient formulations, as well as pipes and/or tubes.

The apparatus may be installed in a fixed location near a target area, for instance, by placing the apparatus within a compartment mounted to a suitable wall. First, the pump inlet and outlet tubing connections for water pump, nutrient pump and air pump to bioreactor, water reservoir and nutrient containers, respectively, are made to the respective bulkhead tube fittings on a manifold or, alternatively, directly to the respective container. Next the electrical connections (heater, air pump, level control and main power cord) to the controller unit are made. Lastly, the effluent/product line is suitably connected to the target system, in a typical restaurant-type kitchen, preferably is tapped directly downstream of the "P" trap in a sink drain. Other suitable methods and styles of installation will occur to those skilled in the art. Preparation for the process of the present invention involves first sterilizing the bioreactor vessel. After the bioreactor is suitably sterilized, a bacterial product is introduced into the bioreactor vessel. The bioreactor vessel is then sealed and all future connections are capped off until after installation. The bioreactor can be easily removed for scheduled service, scheduled replacement, or emergency without removing the whole unit.

The dosing cycles for potable water and nutrient delivery to bioreactor (from the reservoir and nutrient vessel, respectively) are set to the same number of cycles per day, generally 4, 8 to 6, preferably 6 to 12. In a 2 timer embodiment, nutrient delivery to the bioreactor should lag water delivery by 15 to 60 minutes, depending on the spacing of cycles. When used with a formulation the ratio of amount of potable water (by volume) to nutrient should be between 50 to 200, preferably 75 to 125. The requisite ratio may be achieved by calibrating the respective transfer pumps accordingly. The total daily volume of effluent produced is equal to the total daily volume of potable water delivered to the bioreactor.

In operation, the potable water delivered to the bioreactor should be set from about 1 to about 12 times the total volume of bioreactor, preferably from about 2 to about 6 times the volume. The temperature of the bioreactor is set on a heater and should be from about 60 degrees F to about 120 degrees F, preferably from about 80 degrees F to about 100 degrees F.

The process may be initiated by starting water and nutrient flow to the bioreactor. For instance, by cycling the nutrient and water pumps enough times to fill the bioreactor. This, along with the heat and aeration, will start the germination process. After initiation, there will be copious bubbling of the composition in the bioreactor, now inoculated with microbes. The resulting aeration aids the overall growth and colonization of the bacterial species. In time, the bacterial substrate utilization rates (of fats, and also protein and carbohydrates) approach that of delivery rates. The organization of the bacteria consortium will in general continually tend to improve overall over time as the species co-adapt to maximize target type substrate utilization.

The process of the invention involves pumping of nutrients from the nutrient container by a nutrient pumping means into the bioreactor vessel via tubes or pipes. Water flows into the reservoir vessel. The water is pumped from the reservoir vessel via tube/pipe by a water pumping means through tube/pipe into the bioreactor vessel, thus displacing microbes, organic and inorganic nutrients and bacterial products into a target dosing tube/pipe leading out of the bioreactor vessel toward the environment to be treated. This discharge may be timed and/or suitably regulated. The cycle then repeats according to intervals set on the timer(s).

In preparing the bioreactor for the process of the instant invention, the bioreactor compartment is sterilized by cleaning it with, or otherwise applying, a suitable disinfectant agent to the surface. For instance, a 70% ethanol solution, or some similar alcohol based surface active disinfectant may be used. After the bioreactor has been suitably sterilized, a suspended bacterial product, either in desiccated or in liquid spore-like form, is added to the bioreactor compartment. Preferably, the bacterial product is enclosed in a $\frac{1}{16}$ inch steel mesh ball, and contains from about 1 to about 15 grams of bacterial composition. The bioreactor is then sealed and all connections are capped off until after installation.

The microorganisms employed in the starter material may vary upon the type of contaminant to be treated. In one embodiment, where the microorganisms are used to degrade hydrocarbons, i.e. grease, the starter material contains at least one microorganism selected from the group consisting essentially of *Bacillus licheniformis, Bacillus subtilis, Pseudomonas fluorescens E, Pseudomonas putida, Enterobacter cloacae,* and *Bacillus thuringienis*. A preferred bacterial product that may be employed is Bi-Chem® SM 700 from Sybron, Inc., of Salem, Va. which is a blend containing 8 non-pathogenic organisms capable of digesting organic grease and fats. The starter material generally has a concentration of cells of at least $\sim 1 \times 10^8$ per fluid ml as well as the essential inorganic and organic nutrients to maintain the cell culture in the exponential phase of growth. The content and concentration of the inorganic and organic nutrients in the food will vary with the type of microorganism used in the apparatus.

A composition containing organic and inorganic nutrients may be in either a liquid or solid (e.g. powdered) matter state. If a liquid, the formula may have a pre-determined concentration, the preferred concentration is on the order of 100 times. An embodiment of a composition containing organic and inorganic nutrients that is used as part of a starter material generally includes a metal-oleate, preferably K-oleate, and one or more of magnesium sulfate, calcium chloride, potassium phosphate, sodium phosphate, sodium EDTA, sodium hydroxide, ferric NH citrate, potassium bicarbonate, sodium chloride, dextrose, citrate, yeast extract, whey extract, ketrol, ammonium nitrate, ammonium chloride, glycerin, Tween 20, Tween 80, corn oil, Simethlycone, and trace elements that include but are not limited to copper sulfate, cobalt(II) chloride, Sodium EDTA, Molybolic acid, $MnCl_2\text{-}7H_2O$, and zinc sulfate.

Preferably the composition containing organic and inorganic nutrients includes about 50 to about 60 weight % of water, about 20 to about 30 weight % K-oleate, about 2 to about 3 weight % glycerin, about 3 to about 10 weight % of vegetable oil and less than about 1 weight % of compounds selected from the group consisting essentially of $MgSO_4$, $CaCl_2$, $NaHPO_4\text{-}7H_2O$, $K_2HPO_4$, NaCl, Dextrose, Citrate, Yeast Extract, Whey Extract, Trace elements, Sodium EDTA, Keltrol, Ferric NEcitrate, NaOH, $NH_4NO_3$, $NH_4Cl$, Tween 20, Tween 80, and Simetblycone. Most preferably the vegetable oil is a mixture of about 4 to about 5 weight % of corn oil and about 5 to about weight 6% canola oil peanut oil.

The composition containing organic and inorganic nutrients can be prepared by mixing metal-oleate, glycerin, Tween 20, Tween 80, water, and Keltrol in a mixing kettle. $MgSO_4$, $CaCl_2$, Sodium EDTA is added to 1 gallon of water and the pH is brought to about 8 to about 10, preferably about 9 using about 10N NaOH. This mixture is then added to the mixing kettle and is mixed for about 2 minutes. To about 5 gallons of water the $Na_2HPO_4\text{-}H_2O$ and $K_2HPO_4$ is added. The pH is brought to about 8 to about 10, preferably about 9 using about 10N NaOH. This mixture is added to the mixing kettle after 2 minutes of mixing.

The NaCl, Dextrose, Citrate, Yeast Extract, Whey Extract, $NH_4NO_3$, $NH_4Cl$, $CoCl_2.6H_2O$, $CuSO_4$, $Na_2EDTA$, Molybolic Acid, $MnCl_2.4H_2O$, $ZnSO_4.7H_2O$, Vitamin A, Vitamin D, Vitamin E, Vitamin K, Thiamin, Riboflavin, Niacin, Vitamin B6, Folic Acid, Vitamin $B_{12}$, Biotin, Pantothenic Acid, Calcium, Iron, Phosphorous, Iodine, Magnesium, Zinc, Selenium, Copper, Mn, Chromium, Molybdenum, Chloride, Potassium, Boron, Nickle, Silicon, Tin, and Vanadium are mixed in about 8 gallons of water.

In a separate container Sodium EDTA and ferric NHcitrate is dissolved in about 200 ml of hot water and then added to the composition. The 8 gallon mixture brings the pH of the total composition to a pH of from about 9 to about 10, preferably about 9. The mixture is then added to the mixing kettle. Finally, corn oil and canola oil are added to the mixing kettle, and $NH_4NO_3$ and $NH_4Cl$ are sprinkled into the mixing kettle. The combined mixture is mixed thoroughly and filled into a dispensing container immediately. An anti-foaming agent may then be added. The pH of the final mixture should be from about 9 to about 10, preferably from about 9.3 to about 9.6.

As explained above, when the composition is used as a starter material, at least one microorganism is added. The microorganism may be selected from the group of microorganisms (and may consisting essentially of (or consist of) *Bacillus licheniformis, Bacillus subtilis, Pseudomonas fluo-*

*rescens E, Pseudomonas putida, Enterobacter cloacae*, and *Bacillus thuringienis*, and may be added prior to inoculation of the bioreactor. It is within the scope of the invention to substitute microorganism not listed that are capable of digesting waste.

DETAILED DESCRIPTION OF THE DRAWINGS

As illustrated in FIGS. 1 through 4, the apparatus comprises four main subsystems: a controller unit 42; a bioreactor 1; a potable water reservoir and regulator 24, and nutrient container 37.

The controller unit 42 (FIG. 1) houses and protects electronic components and isolates all electrical components, fuses, electrical boards, and connections for safe operation of the system to comply with applicable standards. The controller unit may include a multiplicity of pumps, i.e. pumps (X, Y, and Z), solenoid 43, backflow prevention device 44 and at least one timer (not shown). In an alternative embodiment, the controller may be stand-alone and the pumps independent. The solenoid 43 is regulated by a timer, and peristaltic liquid (nutrient) pump Y and peristaltic liquid (water) pump X may be controlled by separate timer potentiometer devices operating off a single timer located either within the controller or as an external device. Each pump is preferably controlled by an independent timer and each timer is set slightly out of phase from the others.

Figure 1:
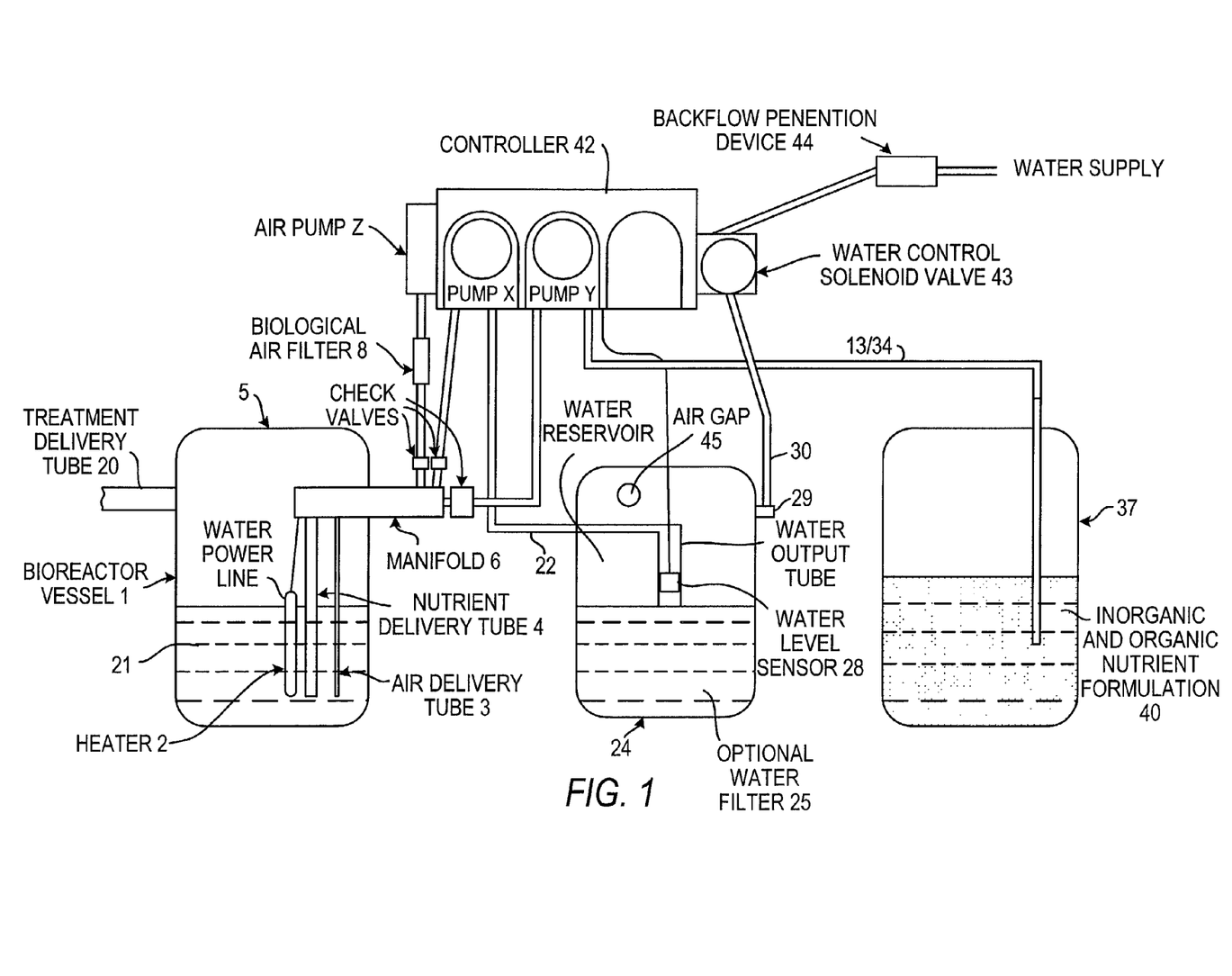
FIG. 1 illustrates a system diagram of one embodiment of the invention.
Figure 2:
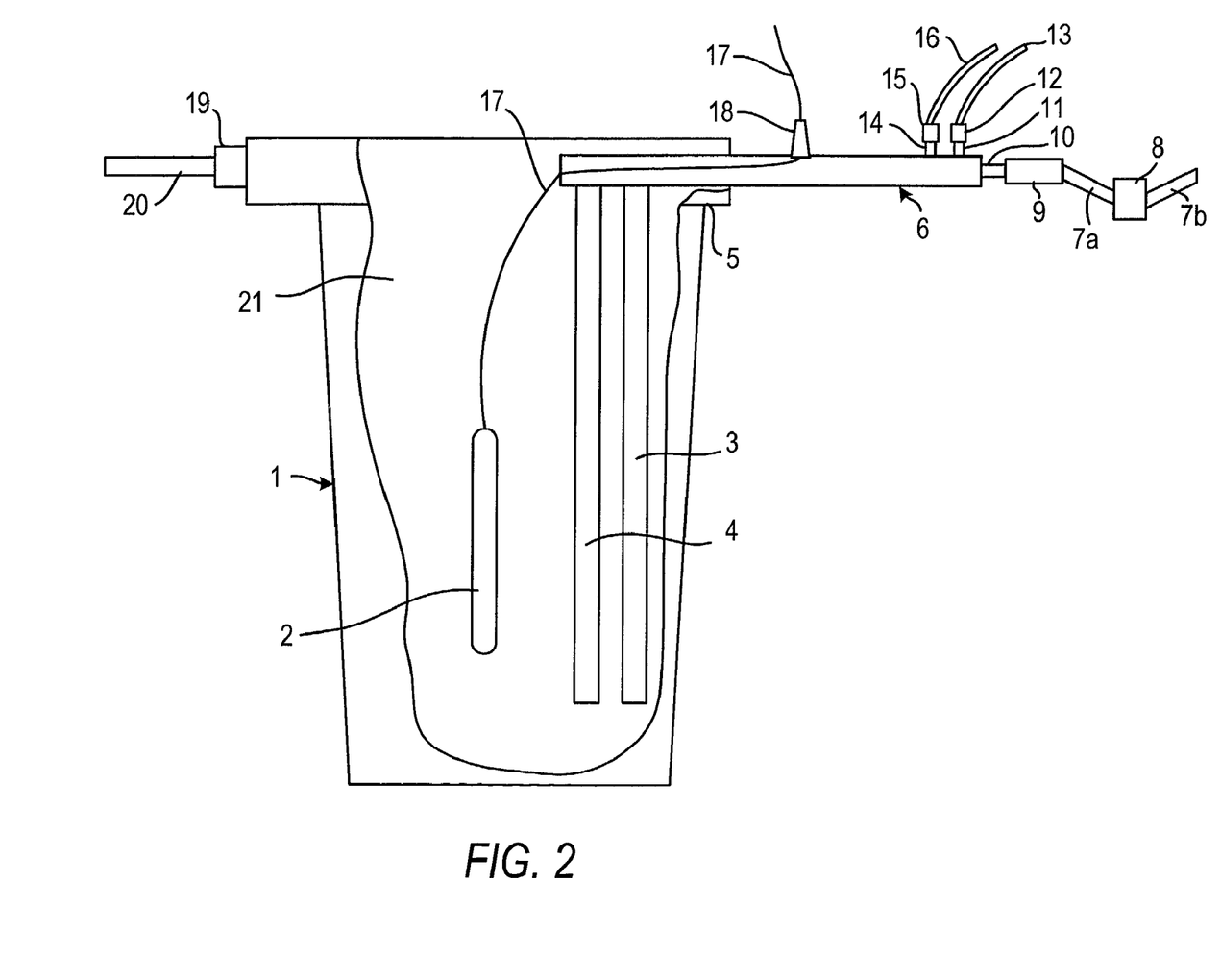
FIG. 2 illustrates a cutaway diagram of the Bioreactor of the embodiment shown in FIG. 1.
Figure 3:
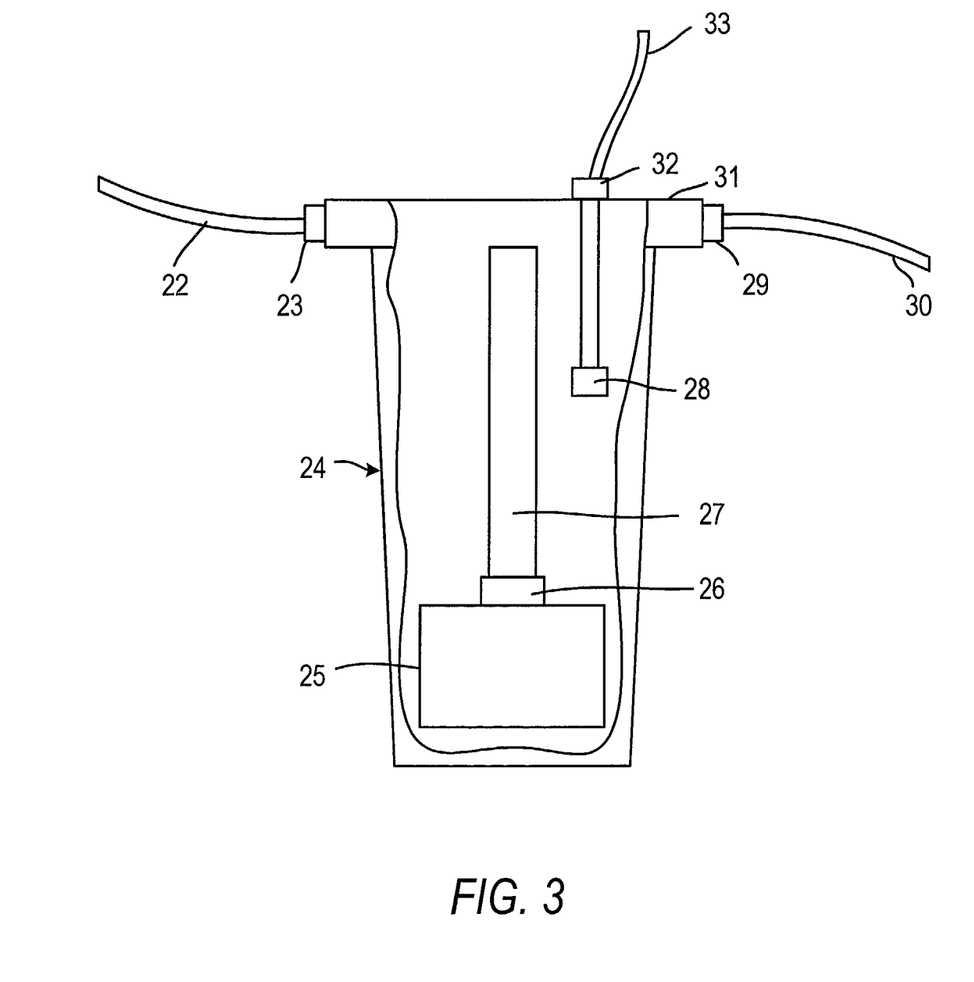
FIG. 3 illustrates a cutaway diagram of the Water Reservoir and Regulator of the embodiment shown in FIG. 1.
Figure 4:
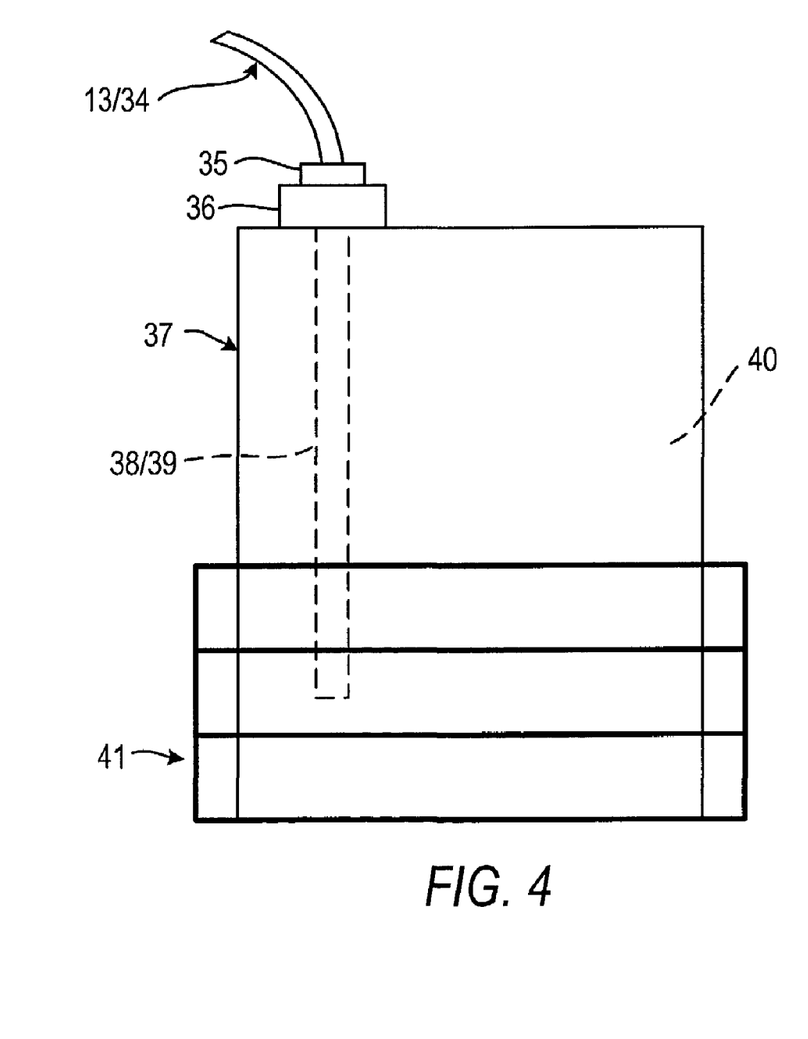
FIG. 4 illustrates a cutaway diagram of the Inorganic and Organic Nutrient container of one embodiment shown in FIG. 1.

The bioreactor 1 includes a vessel for providing an environment conducive for the culturation of microbes. As illustrated in FIGS. 1 and 2, the bioreactor includes a thermostatically controlled heater 2, an aeration tube 3, manifold 6, check valves (9,12 and 15) for isolation, and pipes and/or tubing to provide for aeration and for delivery of the nutrient formulation. In addition, the bioreactor may also include a network of material in the form of a "web" that increases the surface area in the bioreactor so as to enhance bacterial growth. The increased surface area provides additional surface area for the bacterial colonies to attach and flourish.

Potable water reservoir and volume regulator 24 (FIGS. 1 and 3) provides a regulated acclimatized supply of water for bioreactor 1. The reservoir and regulator 24 also dampens external pressure events, isolates the water supply, and regulates the volume of water provided to bioreactor 1 through one or more pumps provided by controller. The reservoir includes a vessel (generally 24), a level sensor 28, tubes and/or pipes (22 and 30), an air gap 45, and a water filtration device (25 and 26) for preconditioning and/or microbial removal from the source water.

Nutrient container 37 (FIGS. 1 and 4) includes a container (generally 37) for organic and inorganic nutrient formulation 40 and has connecting pipes and/or tubes (13/34) that connect to pump Y.

Figure 5:
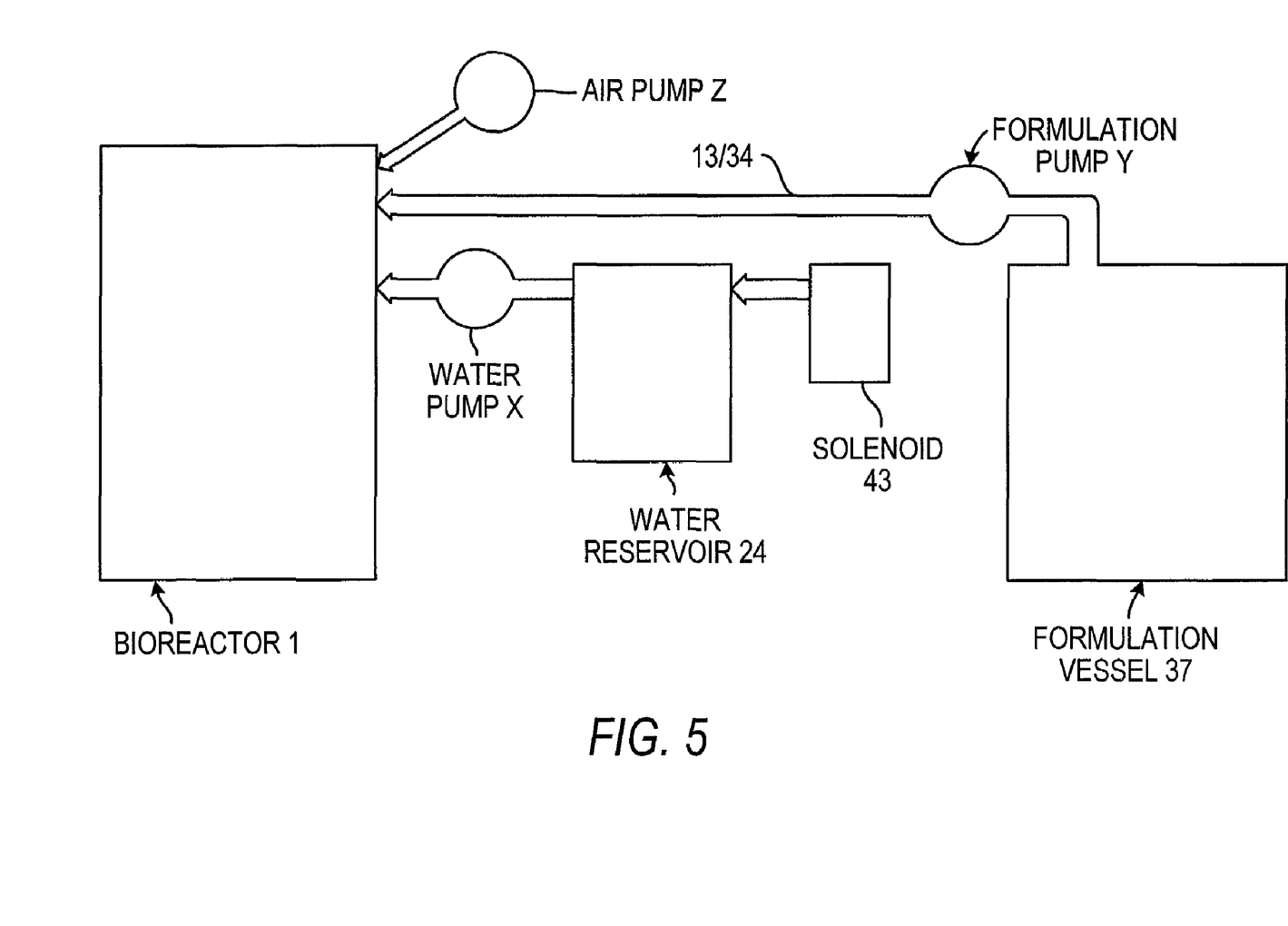
FIG. 5 is a chart illustrating a systems diagram of the embodiment of the invention shown in FIG. 1.
Figure 6:
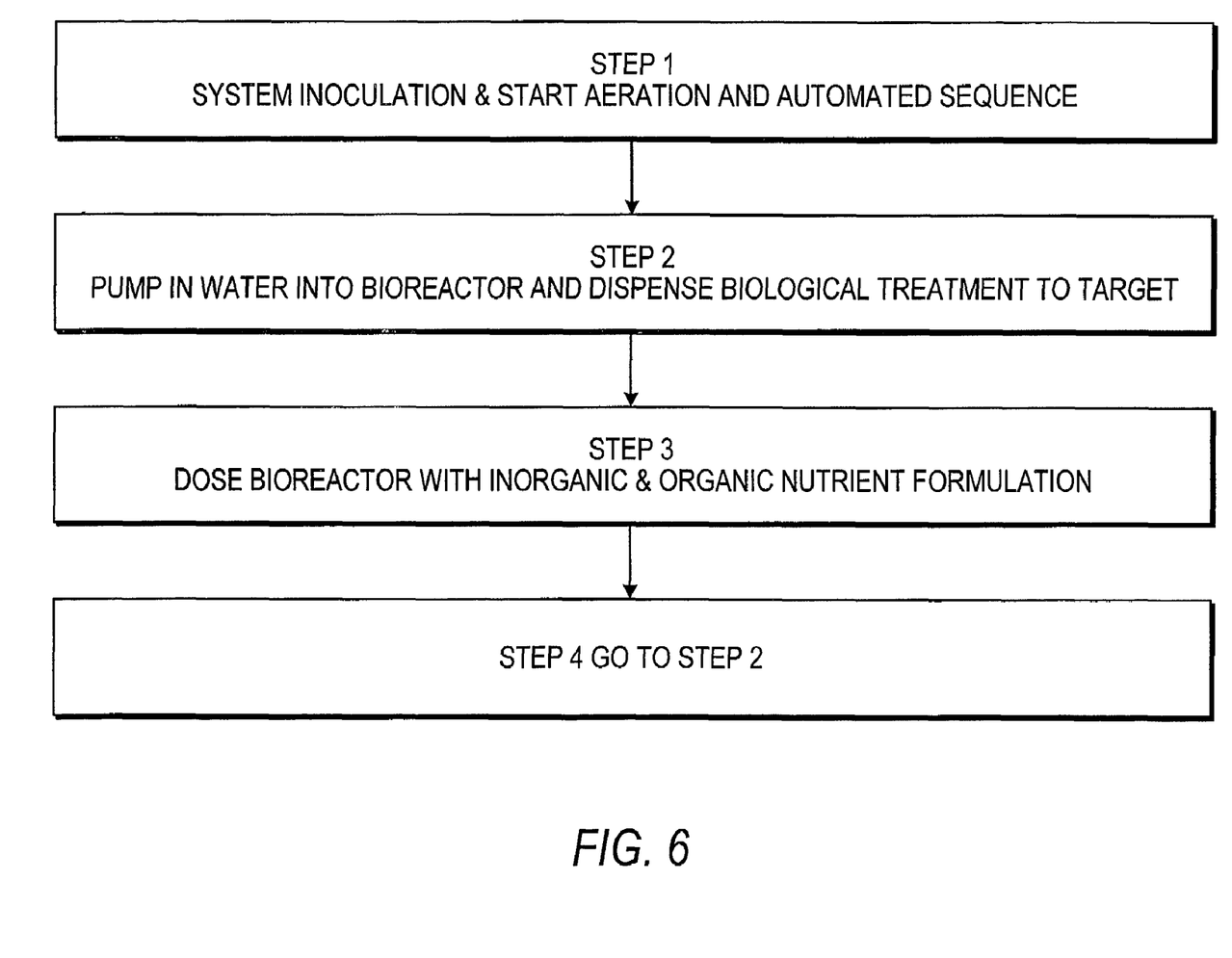
FIG. 6 is a flow chart illustrating a method according to an embodiment of the invention.

The method of the invention is illustrated in the system diagramed in FIG. 5, and summarized as to one embodiment in the flow chart of FIG. 6. The method involves inoculation of the system and the beginning of aeration in bioreactor 1 vessel. Water and nutrient formula flow then starts to bioreactor 1 vessel. This can be done by cycling the nutrient formula and water pumps enough times to fill the vessel. This, along with the heat and aeration, will start the germination process which will require several days before the bacterial species are at full metabolic rate and begin to produce concentrated colonies called "bio-films." The automated process is then started. After initiation, there will be copious bubbling of the formulation, now inoculated with microbes, due to aeration, a process that aids in the overall growth and colonization of the bacterial species. After approximately two weeks, the bubbling will largely subside as the bacterial substrate utilization rates (of fats, and also protein and carbohydrates) approach that of delivery rates. The organization of the bacteria consortium will general continually tend to improve overall over time as the species co-adapt to maximize target-type substrate utilization. The colonies will concentrate on a network of filaments, e.g. a mesh, provided so as to be a highly concentrated aggregate of bacteria. This aggregate may have the appearance of cottage cheese and will provide a high colony count once pushed out of the bioreactor to the area to be treated.

The biomass that is released to the environment to be treated may comprise a self-inoculating bio-film. The bio-film released from the bioreactor comprises a highly concentrated number of bacterial colonies that are acclimated to the environment to be treated and are in logarithmic growth phase. For the purpose of this patent, a colony should be understood to mean a plurality of bacterial cells aggregated together as a unit compared to the same number of bacterial cells existing independently.

As stated above, the bio-film that is produced in the bioreactor may be produced on a bio-mesh or any other internal surface of the bioreactor. A bio-mesh is a network of filaments aggregated together to provide an increased ratio of surface area to volume. As the bioreactor doses bacteria to the environment to be treated only a portion of the bio-film is released into the environment to be treated leaving behind the mother load of bacterium which continues to multiply and provide high volumes of bacterium.

The method of the invention involves pumping of nutrient formulation 40 from nutrient container 37 via tubes or pipes by formulation pump Y through tube or pipe 13 and check valve 12 through manifold 6 into the bioreactor 1 vessel via tube or pipe 4. Tap water flows through the backflow device 44 into the solenoid valve 43 into the reservoir vessel 24 until the level control device 28 de-energizes the solenoid valve 43. The water warms toward room temperature as it remains in the reservoir vessel 24 until the next cycle. The water is pumped from reservoir vessel 24 via tube/pipe 22 by water pump X through tube/pipe 16, check valve 15 into bioreactor 1 vessel via tube/pipe 4, thus displacing microbes, organic and inorganic nutrients and bacterial products 21 into the target dosing tube/pipe 20. Thus discharge of microbes and bacterial products into the target environment proceeds by pressure caused by the build-up of fluid in the bioreactor 1 vessel. This discharge continues as a bubble discharge after the water bubble level reaches equilibrium with the level of target dosing tube 20, as bubble formation waning over time does not affect total dosing amount. Eventually the fluid level in the bioreactor vessel recedes as the timed water flow into bioreactor 1 subsides, and thus no additional fluid is released through the target dosing tube/pipe 20. The cycle then repeats according to intervals set on the timer(s).

While the invention has been illustrated and described with respect to specific illustrative embodiments and modes of practice, it will be apparent to those skilled in the art that various modifications and improvements may be made without departing from the scope and spirit of the invention. Accordingly, the invention is not to be limited by the illustrative embodiment and modes of practice.

DETAILED IDENTIFICATION OF THE COMPONENTS IN THE FIGURES.

1) Bioreactor Vessel
2) Thermostatically Controlled Heater
3) Aeration Tube
4) Water/Nutrient Tube/Pipe
5) Vessel Top
6) Manifold
7a) Air Tube
7b) (Air Tube
8) Biological Air Filter—0.2 PTFE
9) Air Check Valve
10) Fitting
11) Fitting
12) Formulation Check Valve
13) Formulation Tube/Pipe
14) Fitting
15) Water Chock Valve
16) Water Tube
17) Heater Power Cord
18) Electrical Bulkhead Fitting
19) Fitting
20) Target Dosing Tube/Pipe
21) Microbes, Organic and Inorganic Nutrients, water and bacterial products
22) Water Tube/Pipe
23) Fitting
24) Reservoir Vessel
25) Filter
26) Filter Retainer
27) Up Pipe
28) Level Control Device
29) Fitting
30) Water Tube/Pipe from Solenoid
31) Vessel Top
32) Electrical Bulkhead Fitting
33) Level Control Wire
34) Formulation Tube/Pipe
35) Fitting
36) Nutrient container Cap
37) Nutrient container
38) Formulation Up Tube/Pip. I
39) Formulation Up Tube/Pipe 2
40) Organic & Inorganic Nutrient Formulation
41) Rack
42) Controller Unit
43) Water Control Solenoid Valve
44) Back Flow Device
45) Air Gap

What is claimed is:

1. A method for the biological treatment of an environment to be treated comprising:
    continuously dosing a bacterial composition from an apparatus for delivering microorganisms to an environment to be treated wherein the apparatus comprises:
    a bioreactor;
    a nutrient container comprising a mixture of inorganic and organic nutrients;
    a nutrient pumping means for pumping inorganic and organic nutrients from the nutrient container to the bioreactor, the nutrient pumping means is in fluid communication with the nutrient container and the bioreactor; and
    a water pumping means for pumping water into the bioreactor, the water pumping means is in fluid communication with the bioreactor and a water source wherein the water pumped into the bioreactor displaces fluid out of the bioreactor to the environment to be treated.

2. A method for the biological treatment of an environment to be treated according to claim 1 wherein the apparatus further comprises a reservoir in fluid communication with the water source and the water pumping means wherein the nutrient pumping means pumps water from the reservoir to the bioreactor.

3. A method for the biological treatment of an environment to be treated according to claim 1 wherein the apparatus further comprises a controller comprising a controller comprising a programmable memory and an actuator, the controller being in communication with the nutrient and water pumping means wherein the actuator activates the nutrient and water pumping means according to a predetermined schedule stored in the programmable memory of the controller.

4. A method for the biological treatment of an environment to be treated comprising:
    continuously dosing a bacterial composition from an apparatus for delivering microorganisms to an environment to be treated wherein the apparatus comprises:
    a bioreactor comprising an output tube to the environment to be treated;
    a nutrient container comprising a mixture of inorganic and organic nutrients;
    a nutrient pumping means for pumping inorganic and organic nutrients from the nutrient container to the bioreactor, the nutrient pumping means is in fluid communication with the nutrient container and the bioreactor; and
    a solenoid in fluid communication with the water supply and the bioreactor, the solenoid having an open and closed position wherein water flows into the bioreactor when the solenoid is in the open position and water is prevented from entering into the bioreactor when the solenoid is in the closed position.

5. A method for the biological treatment of an environment to be treated according to claim 4 wherein the apparatus further comprises a reservoir, said reservoir in fluid communication with the water supply and the bioreactor wherein water enters the reservoir and flows to the bioreactor once a predetermined level is reached.

6. A method for the biological treatment of an environment to be treated according to claim 4 wherein the apparatus further comprises a controller comprising a programmable memory and an actuator, the controller being in communication with the solenoid and the nutrient pumping means wherein the actuator activates the solenoid and nutrient pumping means according to a predetermined schedule stored in the programmable memory of the controller.

7. A method comprising:
    cycling delivery of nutrients and water according to a predetermined cycling rate to a bioreactor having a bacterial composition, the bioreactor in fluid communication with an environment to be treated; and
    dosing the environment to be treated with at least a portion of the bioreactor bacterial composition.

* * * * *